(12) United States Patent
Hammond

(10) Patent No.: US 6,197,822 B1
(45) Date of Patent: Mar. 6, 2001

(54) NEUROPEPTIDE ANTAGONISTS

(75) Inventor: Marlys Hammond, Salem, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/491,293

(22) Filed: Jan. 25, 2000

Related U.S. Application Data

(60) Provisional application No. 60/117,395, filed on Jan. 27, 1999.

(51) Int. Cl.⁷ .................................................. A61K 31/165
(52) U.S. Cl. ........................................... 514/617; 514/673
(58) Field of Search ..................... 574/617, 635

(56) References Cited

U.S. PATENT DOCUMENTS

| | | | |
|---|---|---|---|
| 5,576,337 | 11/1996 | Bruns, Jr. et al. | 514/324 |
| 6,048,900 | * 4/2000 | Connell et al. | 514/663 |

FOREIGN PATENT DOCUMENTS

| | | | |
|---|---|---|---|
| 0759441 | 2/1997 | (EP) | C07K/14/47 |
| WO9614307 | 5/1996 | (WO) | C07D/295/02 |

OTHER PUBLICATIONS

Wahlestedt et al, *Regul. Peptides*, 13: 307–318 (1986).
McCauley and Westfall, *J. Pharmacol. Exp. Ther.* 261:863–868 (1992).
Grundemar et al, *Br. J. Pharmacol.* 105:45–50 (1992).
Flood and Morley, *Peptides*, 12:1251–1260 (1991).
Leibowitz and Alexander, *Peptides*, 12:1251–1260 (1991).
Stanley et al, *Peptides*, 13:581–587 (1992).
Grundemar and Hakanson, *TIPS*, May 1994 [vol. 15], 153–159.
Muramatsu, et al, *Tetrahedron Letters* No. 23, pp. 2133–2136 (1973).
Stevens and French, *J. Am. Chem. Soc.* 1953, 75, 657–60.
Hoerhold and Eibish, *Tetrahedron 1969*, 25, 4277–4286.
Gordon et al, *Journal Neurochem.* 55:506–513, 1990.

* cited by examiner

Primary Examiner—James H. Reamer
(74) Attorney, Agent, or Firm—Peter C. Richardson; Gregg C. Benson; Mervin E. Brokke

(57) ABSTRACT

The compound

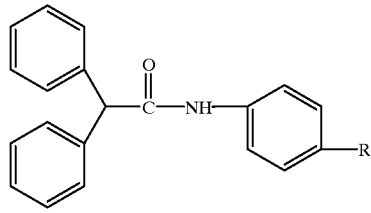

is a neuropeptide Y antagonist and is effective in treating feeding disorders, cardiovascular diseases and other physiological disorders.

4 Claims, No Drawings

NEUROPEPTIDE ANTAGONISTS

This application is filed claiming priority from co-pending Provisional Application No. 60/117,395 filed Jan. 27, 1999.

BACKGROUND OF INVENTION

1. Field of the Invention

This invention relates to the use of diphenylacetanilides which selectively bind to mammalian Neuropeptide receptors. It further relates to the use of these compounds and compositions containing these compounds in treating conditions related to an excess of neuropeptide Y such as feeding disorders and certain cardiovascular diseases.

2. Description of the Related Art

Neuropeptide Y, a peptide first isolated in 1982, is widely distributed in the central and peripheral neurons and is responsible for a multitude of biological effects in the brain and the periphery. Various animal studies have shown that activation of neuropeptide Y1 receptors is related to vasoconstriction, Wahlestedt et al *Regul. Peptides,* 13: 307–318 (1986), McCauley and Westfall, *J. Pharmacol. Exp. Ther.* 261:863–868 (1992), and Grundemar et al *Br. J. Pharmacol.* 105:45–50 (1992); and to stimulation of consummatory behavior, Flood and Morley, *Peptides,* 10:963–966 (1989), Leibowitz and Alexander, *Peptides,* 12:1251–1260 (1991), and Stanley et al *Peptides,*.13:581–587 (1992).

Grundemar and Hakanson *TIPS,* May 1994 [Vol. 15], 153–159, state that, in animals, neuropeptide Y is a powerful stimulus of food intake, and an inducer of vasoconstriction leading to hypertension. They further point out that low levels of neuropeptide Y (NPY) are associated with loss of appetite. These reports clearly indicate that compounds that inhibit the activity of this protein will reduce hypertension and appetite in animals.

EP0759441 and U.S. Pat. No. 5,576,337 report that physiological disorders caused by neuropeptide Y include:
disorders or diseases pertaining to the heart, blood vessels or the renal system, such as vasospasm, heart failure, shock, cardiac hypertrophy, increased blood pressure, angina, myocardial infarction, sudden cardiac death, arrhythmia, peripheral vascular disease, and abnormal renal conditions such as impaired flow of fluid, abnormal mass transport, or renal failure; conditions related to increased sympathetic nerve activity for example, during or after coronary artery surgery, and operations and sugery in the gastrointestinal tract;
cerebral diseases and diseases related to the central nervous system, such as cerebral infarction, neurodegeneration, epilepsy, stroke, and conditions related to stroke, cerebral vasospasm and hemmorrhage, depression, anxiety, schizophrenia, and dementia;
conditions related to pain or nociception;
diseases related to abnormal gastrointenstinal motility and secretion, such as different forms of ileus, urinary incontinence, and Crohn's disease;
abnormal drink and food intake disorders, such as anorexia and metabolic disorders;
diseases related to sexual dysfunction and reproductive disorders;
conditions or disorders associated with inflammation;
respiratory diseases, such as asthma and conditions related to asthma and bronchoconstriction; and diseases related to abnormal hormone release, such as leutinizing hormone, growth hormone, insulin, and prolactin.

WO 96/14307 refers to substituted benzylamine derivatives which selectively bind to human neuropeptide Y1 receptors.

SUMMARY OF THE INVENTION

This invention comprises a method of inhibiting or alleviating a pathological condition or physiological disorder in a mammal characterized by or associated with neuropeptide Y which comprises administering to a mammal in need of such treatment a neuropeptide Y inhibiting amount of the compound of the formula:

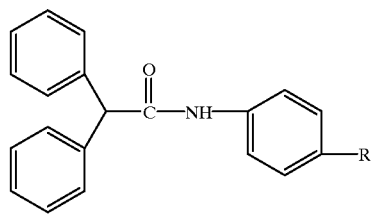

I wherein R is —N(C$_2$H$_5$)$_2$

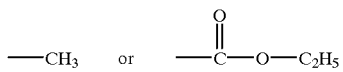

or a pharmaceutically acceptable salt thereof

In another aspect, this invention comprises a method of inhibiting or alleviating a pathological condition or physiological disorder in a mammal characterized by or associated with an excess of neuropeptide Y which accompanies administering to a mammal in need of such treatment a neuropeptide Y inhibiting amount of the compound of Formula I shown above.

This invention also comprises a method of treating a pathological condition wherein said pathological condition or physiological disorder is a feeding disorder such as obesity or bulimia.

In another aspect, this invention comprises a method of inhibiting or alleviating a pathological condition or physiological disorder in a mammal wherein said pathological condition or physiological disorder is selected from the group consisting of:
disorders or diseases pertaining to the heart, blood vessels or the renal system, such as vasospasm, heart failure, shock, cardiac hypertrophy, increased blood pressure, angina, myocardial infarction, sudden cardiac death, arrhythmia, peripheral vascular disease, and abnormal renal conditions such as impaired flow of fluid, abnormal mass transport, or renal failure;
conditions related to increased sympathetic nerve activity for example, during or after coronary artery surgery, and operations and surgery in the gastrointestinal tract;
cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, and dementia;
conditions related to pain or nociception;
diseases related to abnormal gastrointenstinal motility and secretion, such as different forms of ileus, urinary incontinence, and Crohn's disease;
abnormal drink and food intake disorders, such as anorexia and metabolic disorders;
diseases related to sexual dysfunction and reproductive disorders;
conditions or disorders associated with inflammation;
respiratory diseases, such as asthma and conditions related to asthma and bronchoconstriction; and diseases related to abnormal hormone release, such as leutinizing hormone, growth hormone, insulin, and prolactin.

The compound of formula I when R is —$N(C_2H_5)_2$ is basic in nature and capable of forming a wide variety of salts with various inorganic and organic acids. The acids that may be used to prepare pharmaceutically acceptable acid addition salts of the compound of formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, fumarate, gluconate, glucaronate, saccharate, formate, benzoate, glutamate, methanesulfonate, ethanesulfonate, benzenesulfonate, and p-toluenesulfonate.

DETAILED DESCRIPTION OF THE INVENTION

The compounds of formula I are known in the chemical literature and may be prepared by the procedures described Muramatsee, et al. *Tetrahedron Letters* No. 23, pp. 2133–2136 (1973); Stevens and French, *J. Am. Chem. Soc.* 1953, 75, 657–60; and Hoerhold and Eibish, *Tetrahedron* 1969, 25, 4277–4286. These references are hereby incorporated by reference.

Briefly, the compound of formula I wherein R is —$N(C_2H_5)_2$ is prepared by irradiation of molar equivalents of diphenyidiazomethane and p-diethylamino-phenyl isonitrile. The compound of formula I is a colorless solid, mp 145–6° C.

The acid addition salts of this compound are readily prepared by treating the base compound with a substantially equivalent amount of the chosen mineral or organic acid in an aqueous solvent or suitable organic solvent such as methanol or ethanol. Upon evaporation of the solvent, the derived salt is obtained.

The pharmaceutical utility of the compound of Formula I is indicated by the following assays for human NPY1 and NPY5 receptor activity.

NPY1 Assay

The procedure used is similar to that described by Gordon et al. (*J. Neurochem.* 55:506–513, 1990). SK-N-MC cells were purchased from ATCC (Rockville, Md.). Cells were maintained at 37° C. and 5% $CO_2$ in Dulbecco's modified essential media (DMEM) with L-glutamine and 110 mg/L sodium pyruvate, which was supplemented with 10% fetal bovine serum and 25 mM HEPES (pH 7.3). The binding assay was performed in 24-well plates (Falcon) when the cells were confluent. Taking care to not disturb the cells on the bottom of the wells, the media was aspirated, and 0.5 ml of Dulbecco's phosphate buffered saline (DPBS) with calcium and magnesium were added to each well. The DPBS was aspirated and an additional aliquot of DPBS was added and aspirated. To begin the assay, binding buffer consisting of serum-free DMEM containing 0.5% bovine serum albumin, 0.1% bacitracin and 0.1 mM phenylmethylsulfonylfluoride was added to each well. The cells and the binding buffer preincubated for 30 minutes at room temperature, at which point the drug dilution and [$^{125}$I)]PYY (NEN-DuPont: 50000–75000 cpm ~50 pM) were added to yield a final volume of 250 ul. Nonspecific binding was defined with 1 mM NPY (porcine or human, Bachem Calif.). After a 3 hour incubation at room temperature, the plates were then put on ice and the wells were aspirated. The cells were washed 4–6 times with 0.5 ml of ice-cold DPBS. A dilute solution of Triton X-100 (1%) was then added to each well. After approximately 1 hour at room temperature, an aliquot from each well was transferred to a 12×75 mm test tube, and the amount of [$^{125}$I] was quantitated on a gamma counter with an efficiency of 80–85% (Genesys 5000, Laboratory Technologies). $IC_{50}$ values were calculated with the non-linear curve fitting program RS/1 (BBN Software Products Corp., Cambridge, Mass.).

Assay for NPY-5 Binding

[$^{125}$I]PYY Binding at Human NPY Receptors Expressed in Sf9 Cells

Baculovirus-infected Sf9 cells expressing recombinant human NPY 5 receptors are harvested at 48 hours. At the time of harvest, cell pellets are resuspended in lysis buffer (20 mM Tris-HCl, pH 7.4, 5 mM EDTA, 0.5 μg/ml leupeptin, 2 μg/ml Aprotonin and 200 mM PMSF) and homogenized using a Polytron (setting 3, 25–30 seconds). Homogenates are centrifuged at 4° C. for 5 minutes at 200 x g (~1.5 rpm) to pellet the nuclei. The supernatant is collected into a fresh tube and centrifuged at 48,000 x g for 10 minutes. Pellets are washed once in lysis buffer and centrifuged. The final pellet is resuspended in PBS and stored in aliquots at −80° C. Purified membranes are washed using PBS and resuspended in binding buffer (50 mM Tris(HCl), pH 7.4, 5 mM KCl, 120 mM NaCl, 2 mM $CaCl_2$, 1 mM $MgCl_2$, 0.1% bovine serum albumin (BSA)). Membranes (20 μg/reaction tube) are added to polypropylene tubes containing 0.035 nM [$^{125}$I]PYY(porcine), displacers ranging from $10^{-12}$ M to $10^{-5}$ M, and buffer to yield a final volume of 0.5 mL. Nonspecific binding is determined in the presence of 1 μM NPY(human) and accounts for 10% of total binding. Following a 2 hour incubation at room temperature, the reaction is terminated by rapid vacuum filtration. Samples are filtered over presoaked GF/C Whatman filters (1.0% polyethylenemine) and rinsed 2 times with 5 mL cold binding buffer without BSA. A gamma counter is used to count filters with an efficiency of 85%. $IC_{50}$ values were calculated with the non-linear curve fitting program RS/1 (SigmaPlot, Jandel).

Compounds of Formula I showed the following binding constants in the NPY5

| R | Ki nM |
|---|---|
| —$N(C_2H_5)_2$ | 8 |
| —$CH_3$ | 800 |
| —$COC_2H_5$ (C=O) | 14 |

Functional Assay for NPY Receptors Expressed in Oocytes

Experiments were performed on Xenopus oocytes. Oocytes were prepared and maintained using standard protocols (Dascal and Lotan, in *Methods in Molecular Biology; Protocols in Molecular Neurobiology*, eds. Longstaff & Revest, Humana, Clifton, N.J., 13:1992). For the present experiments, oocytes were obtained from 6 frogs. Oocytes were recorded from 2–7 days following coinjection of GIRK1 and the H17 NPY-1 or NPY-5 subtype mRNA (25 ng of each, 50 nL total volume).

Two electrode voltage clamp recordings were carried out using a Warner Instruments Oocyte clamp OC 725B. Data were collected on a Macintosh microcomputer and analyzed using Superscope software. Voltage and current electrodes were pulled from glass tubing (1.5 mM O.D.) on a Brown/Flaming micropipet puller (Sutter Instruments, model P-87). Electrodes contained 3M KCl and had resistances of 0.5–2 MOhms. Oocytes were bathed in normal external solution containing; 90 mM NaCl, 1 mM KCl, 1 mM $MgCl_2$, 1 mM $CaCl_2$, 5 mM HEPES, pH=7.4. Before NPY agonists or antagonists were introduced, a high $K^+$ solution containing; 1 mM NaCl, 90 mM KCl, 1 mM $MgCl_2$, 1 mM $CaCl_2$, 5 mM HEPES was applied to permit recording of the inwardly rectifying $K^+$ current. Drugs were applied diluted in the high $K^+$ media.

100 $\mu$M stocks of NPY, PP or NPY peptide fragments or PYY peptide fragments were prepared in water and frozen until needed.

Oocytes were voltage-clamped at −80 mV with two electrodes. Oocytes were initially superfused with normal external medium (approximate flow rate 4 ml/min.). Before drugs were applied, cells were superfused with high $K^+$ solution to permit activation of the inwardly rectifying $K^+$ current. In oocytes coinjected with NPY receptor and GIRK1 mRNA, the NPY agonist induced an additional inward current over the resting $K^+$ current caused by high $K^+$ medium. Because responses desensitized at slow, but varying rates, cumulative dose applications were administered to generate concentration response curves. Two to four doses of agonist were applied to each cell. Agonist dose responses in each cell were normalized against the response to a maximal concentration of human NPY. Dose response curves were fit with a logistic equation using Kaleidagraph software (Abelbeck software, Reading, Pa.).

The compound of formula I or a pharmaceutically acceptable salt thereof (the active compound) may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. The active compound may be present in association with one or more non-toxic pharmaceutically acceptable carriers and/or diluents and/or adjuvants and if desired other active ingredients. The pharmaceutical compositions containing the active compound may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active compound in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The active compound may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

The active compound may be administered parenterally in a sterile medium, The drug, depending on the vehicle and concentration used can either be suspended or dissolved in the vehicle. Advantageously, adjuvants such as local anesthetics, preservatives and buffering agents can be dissolved in the vehicle.

Dosage levels of the order of from about 0.1 mg to about 15 mg of active compound per kilogram of body weight per day are useful in the treatment of the above-indicated conditions (about 7 mg to about 1 g per human patient per day). The amount of active compound that may be combined with the carrier materials to produce a single dosage form will vary depending upon the host treated and the particular mode of administration. Dosage unit forms will generally contain between from about 1 mg to about 500 mg of an active compound.

It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

As a consequence of its action in treating pathological conditions the compound of the present invention possess utility for treatment of ungulate animals such as swine, cattle, sheep, and goats. The active compound of the invention can additionally be used for the treatment of household pets, for example companion animals such as dogs and cats. The administration of the active compound of formula I can be effected orally or parenterally. An amount of the active compound of formula I is administered such that an effective dose is received, generally a daily dose which, when administered orally to an animal is usually between 0.01 and 20 mg/kg of body weight, preferably between 0.05 and 10 mg/kg of body weight. Conveniently, the medication can be carried in drinking water so that a therapeutic dosage of the agent is ingested with the daily water supply. The agent can be directly metered into drinking water, preferably in the form of a liquid, water-soluble concentrate (such as an aqueous solution of a water soluble salt).

Conveniently, the active compound can also be added directly to the feed, as such, or in the form of an animal feed supplement, also referred to as a premix or concentrate. A premix or concentrate of therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the active materials in the finished feed with which the premix is blended. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound according to the invention. The mixtures are thoroughly blended by standard procedures, such as in a twin shell blender, to ensure homogeneity.

If the supplement is used as a top dressing for the feed, it likewise helps to ensure uniformity of distribution of the active material across the top of the dressed feed.

Drinking water and feed effective for treating domestic animals are generally prepared by mixing the compound of the invention with a sufficient amount of animal feed to provide from about $10^{-3}$ to 500 ppm of the compound in the feed or water.

The preferred medicated swine, cattle, sheep and goat feeds generally contain from 1 to 400 grams of active compound per ton of feed, the optimum amount for these animals usually being about 50 to 300 grams per ton of feed.

The preferred poultry and domestic pet feeds usually contain about 1 to 400 grams and preferably 10 to 400 grams of active compound per ton of feed.

For parenteral administration in animals, the compounds of the present invention may be prepared in the form of a paste or a pellet and administered as an implant, usually under the skin of the head or ear of the animal in which increase in lean meat deposition and improvement in lean meat to fat ratio is sought.

In general, parenteral administration involves injection of a sufficient amount of the compound of the present invention to provide the animal with 0.01 to 20 mg/kg/day of body weight of the active ingredient. The preferred dosage for poultry, swine, cattle, sheep, goats and domestic pets is in the range of from 0.05 to 10 mg/kg/day of body weight of active ingredient.

What is claimed is:

1. A method of inhibiting or alleviating a pathological condition or physiological disorder in a mammal characterized by or associated with neuropeptide Y which comprises administering to a mammal in need of such treatment a neuropeptide Y inhibiting amount of the compound of the formula:

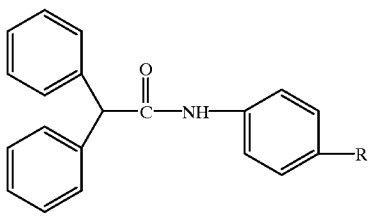

wherein R is selected from —N(C$_2$H$_5$)$_2$, —CH$_3$ and

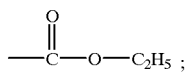

or a pharmaceutically acceptable salt thereof.

2. A method of claim 1 wherein said pathological condition or physiological disorder is a feeding disorder such as obesity or bulimia.

3. A method of claim 1 wherein said pathological condition or physiological disorder is selected from the group consisting of:

disorders or diseases pertaining to the heart, blood vessels or the renal system, such as vasospasm, heart failure, shock, cardiac hypertrophy, increased blood pressure, angina, myocardial infarction, sudden cardiac death, arrhythmia, peripheral vascular disease, and abnormal renal conditions such as impaired flow of fluid, abnormal mass transport, or renal failure;

conditions related to increased sympathetic nerve activity for example, during or after coronary artery surgery, and operations and surgery in the gastrointestinal tract; cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, and dementia;

conditions related to pain or nociception; diseases related to abnormal gastrointenstinal motility and secretion, such as different forms of ileus, urinary incontinence, and Crohn's disease;

abnormal drink and food intake disorders, such as anorexia and metabolic disorders;

diseases related to sexual dysfunction and reproductive disorders;

conditions or disorders associated with inflammation;

respiratory diseases, such as asthma and conditions related to asthma and bronchoconstriction; and diseases related to abnormal hormone release, such as leutinizing hormone, growth hormone, insulin, and prolactin.

4. A pharmaceutical composition for inhibiting or alleviating a pathological condition or physiological disorder in a mammal characterized by or associated with an excess of neuropeptide Y, which comprises the compound of the formula:

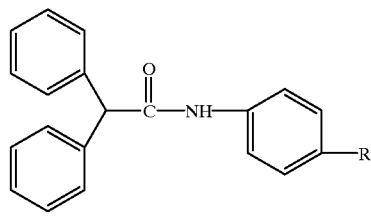

wherein R is selected from —N(C$_2$H$_5$)$_2$, —CH$_3$ and

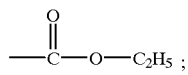

or a pharmaceutically acceptable salt thereof.

* * * * *